United States Patent
Song

(10) Patent No.: US 7,253,644 B2
(45) Date of Patent: Aug. 7, 2007

(54) APPARATUS AND METHOD FOR MEASURING ELECTROCHEMICAL AND VISCOELASTIC PROPERTIES OF A LIQUID

(75) Inventor: Limin Song, Princeton Junction, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 45 days.

(21) Appl. No.: 11/090,631

(22) Filed: Mar. 25, 2005

(65) Prior Publication Data

US 2005/0263409 A1    Dec. 1, 2005

Related U.S. Application Data

(60) Provisional application No. 60/576,055, filed on Jun. 1, 2004.

(51) Int. Cl.
*G01R 27/26*    (2006.01)
(52) U.S. Cl. .................................. 324/698; 324/691
(58) Field of Classification Search ............... 324/698, 324/691
See application file for complete search history.

(56) References Cited

U.S. PATENT DOCUMENTS

| | | | |
|---|---|---|---|
| 5,734,098 A | 3/1998 | Kraus et al. ............... 73/61.62 |
| 6,247,354 B1 | 6/2001 | Vig et al. ................... 73/54.41 |
| 6,260,408 B1 | 7/2001 | Vig et al. ................... 73/64.53 |
| 6,543,274 B1 | 4/2003 | Herrmann et al. ........... 73/32 A |
| 2004/0085080 A1* | 5/2004 | Schilowitz et al. ......... 324/698 |
| 2004/0235198 A1* | 11/2004 | Marx et al. ................. 436/527 |

FOREIGN PATENT DOCUMENTS

| WO | WO 02/065086 A2 | 8/2002 |
|---|---|---|
| WO | WO 03/054482 A2 | 7/2003 |

OTHER PUBLICATIONS

Andrea Sabot and Steffi Krause, Simulataneous Quartz Crystal Microbalance Impedance and Electrochemical Impedance Measurements. Invenstigationm into the Degradation of Thin Ploymer Films; Analytical Chemistry, vol. 74, No. 14, Jul. 15, 2002.*
S. Zabarnick, "Studies of Jet Fuel Thermal Stability and Oxidation Using a Quartz Crystal Microbalance and Pressure Measurements", *Ind. Eng. Chem. Res.*, 1994, 33, pp. 1348-1354.
S. Zabarnick, et al., "Studies of Jet Fuel Additives Using the Quartz Crystal Microbalance and Pressure Monitoring at 140° C.", *Ind. Eng. Chem. Res.*, 1994, 33, pp. 2771-2777.
E.A. Klavetter, et al., "Monitoring Jet Fuel Thermal Stability Using a Quartz Crystal Microbalance", *Energy & Fuels*, 1993, 7, pp. 582-588.

* cited by examiner

*Primary Examiner*—Walter Benson
(74) *Attorney, Agent, or Firm*—Gary P. Katz; Estelle C. Bakun

(57) ABSTRACT

An apparatus for measuring electrochemical and viscoelastic properties of a liquid includes two sensing components, an electrochemical impedance spectroscopy component and a quartz crystal microbalance component positioned within a housing for receiving a liquid for monitoring and arranged so that each component shares a common electrode. Means are provided to simultaneously apply a sinusoidal waveform across the electrodes whereby information on the electrochemical and viscoelastic properties of a liquid being monitored is obtained.

12 Claims, 8 Drawing Sheets

Equivalent Circuit Model

Nyquest Plot

At Point $P_l$ where $X=-R$ $\omega = \omega_l$ $G_l = 1/R_{oil} + 1/(2R)$ $B_l = \omega_l(C_{oil} + C_0) + 1/(2R)$ At Point $P_r$ where $X=0$ $\omega = \omega_r$ $G_r = 1/R_{oil} + 1/R$ $B_r = \omega_r(C_{oil} + C_0)$ At Point $P_u$ where $X=R$ $\omega = \omega_u$ $G_u = 1/R_{oil} + 1/(2R)$ $B_u = \omega_u(C_{oil} + C_0) - 1/(2R)$

APPARATUS AND METHOD FOR MEASURING ELECTROCHEMICAL AND VISCOELASTIC PROPERTIES OF A LIQUID

This application claims the benefit of U.S. Ser. No. 60/576,055 filed Jun. 1, 2004.

FIELD OF THE INVENTION

The invention relates generally to a sensor for measuring the electrochemical and viscoelastic properties of a liquid, and to a method for performing this measurement. More particularly, the invention is directed toward the simultaneous measurement of the electrochemical and viscoelastic properties of a liquid.

BACKGROUND OF THE INVENTION

It is well known that the efficacy of lubricating compositions deteriorates over time as a result of exposure to thermal, oxidative and other environmental stresses. In order to avoid decreased performance, excessive wear and possible component failure of mechanical equipment as a result of using a lubricant beyond its effective life it is necessary to conservatively schedule lubricant change intervals or to resort to frequent sampling and analysis of the lubricant.

In industrial environments oil analysis constitutes an important role in preventive maintenance programs. This analysis, however, typically is conducted off-site and results are not normally available as soon as desirable. Thus, there is a need for a liquid monitoring system that can be conducted continuously on-line.

One approach to a more continuous monitoring of a liquid's quality is to measure the properties of the liquid by an electrochemical impedance technique; and currently there are commercially available sensors for making such measurements. Unfortunately results can be problematic because a viscosity change in the fluid being measured could result in a change in the fluids conductivity.

Presently there are a number of different types of instruments and methods for liquid viscosity measurements, most of which are not suitable for on-line measurements. However, quartz crystal microbalances are commercially available for measuring the viscoelastic properties of a liquid and have been suggested for use in on-line situations.

At present there has yet to be devised a commercially acceptable sensor, or system that is capable of simultaneously monitoring the electrochemical and viscoelastic properties of a lubricant. Thus there remains a need for a method and device, or system, that can simultaneously monitor the electrochemical and viscoelastic properties of a lubricant, or other liquid hydrocarbons.

An object of the present invention is to provide a single sensor that can simultaneously measure the electrochemical impedance and viscosity of a lubricant.

Another object of the invention is to provide a single sensor that can discriminate between viscosity information and electrochemical measurements.

Yet another object of the invention is to provide a simple data analysis method to separate the viscoelastic and electrochemical measurements.

Other objects and advantages of the invention will become apparent upon a reading of the description which follows.

SUMMARY OF THE INVENTION

Accordingly, the present invention provides a single sensor for simultaneously measuring the electrochemical and viscoelastic properties of a liquid such as a lubricant and hereinafter referred to as such for convenience. Simply stated the sensor comprises two sensing components: an electrochemical impedance spectroscopy (EIS) component and a quartz crystal microbalance (QCM) component positioned within a housing for receiving a lubricant for monitoring and arranged so that each component shares a common electrode. The common electrode is spaced apart from non-common EIS electrode thereby defining a space for the lubricant received within the housing. Means are provided to simultaneously apply a sinusoidal waveform across the electrodes of the EIS component and the QCM component for producing a signal whereby information on the electrochemical and viscoelastic properties of any lubricant contained in the sensor is obtained.

In an embodiment of the invention the sensor device is used to measure the electrical conductance and susceptance of an oil by imposing an AC signal at any two of the mechanical resonance point $P_r$, and half power points $P_l$ and $P_u$ at which the vibration power of the crystal is half that of the resonance; and comparing the conductance and susceptance to predetermined conductance and susceptance whereby an indication of the electrochemical and viscoelastic properties of the oil is determined.

Other embodiments of the invention and advantages thereof will be readily understood from a reading of the detailed description in light of the accompanying figures.

DETAILED DESCRIPTION OF THE INVENTION

Figure 1:
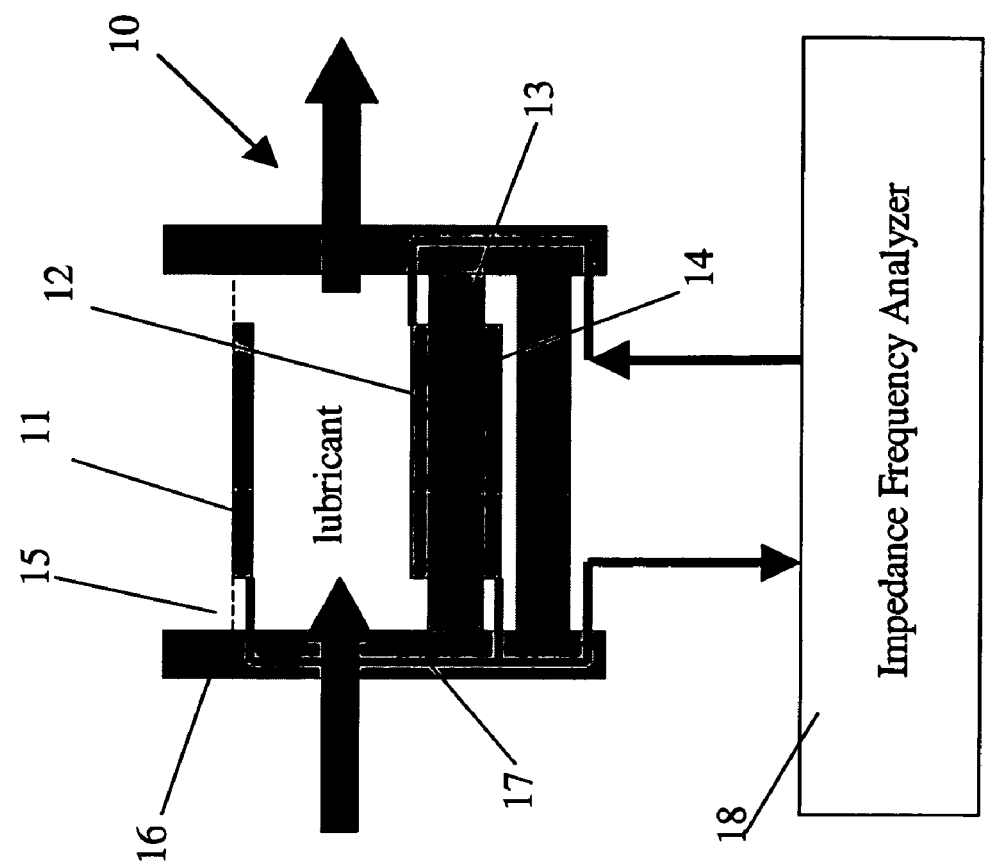
FIG. 1 is a schematic illustration of a two component sensor device of the present invention.

FIG. 1 is a schematic illustration of the sensor of the invention which can be packaged to be placed, for example, within a mechanical system, for example, in an oil reservoir or sump of a mechanical system (not shown), in an oil delivery manifold or bypass manifold of a mechanical system (also not shown) requiring lubrication or use of a working fluid requiring monitoring.

As shown in FIG. 1, the sensor 10 has a housing 16 in which is positioned a quartz crystal 13. Quartz crystal 13 is one typically used in QCM such as an AT-cut quartz resonator. As can be seen crystal 13 has a top electrode 12 and a bottom electrode 14 deposited on the top and bottom surfaces respectively of the quartz crystal. Spaced apart from the top electrode 12 is electrode 11 supported by support member 15 defining a space with housing 16 for receipt of lubricant to be monitored under conditions of use. Bold arrows 20 represent one possible flow direction of lubricant through housing 16.

The dimensions of the electrodes and the spacing of electrodes 11 and 12 will depend on their positioning within the mechanical system and the nature of the working fluid being analyzed. For industrial lubricants, such as paper machine oils, the area of the electrodes typically will be in the range of about 0.1 to about 5 cm$^2$ and the spacing of electrodes 11 and 12 will be between 1 to about 10 mm.

Electrical leads 17 and 19 operatively connect electrodes 11, 12 and 14 to means 18, such as an impedance frequency analyzer, for simultaneously applying a sinusoidal waveform across the electrodes swept over a predetermined frequency range centered at the resonance frequency of the quartz crystal. The applied signal produces an electrical output which is measured and analyzed. Such devices are commercially available and are used to acquire frequency dependent impedance data.

In the arrangement shown electrode 12 is common to both the QCM sensing component and the EIS sensing component of the sensor 10 of the invention.

Figure 2:
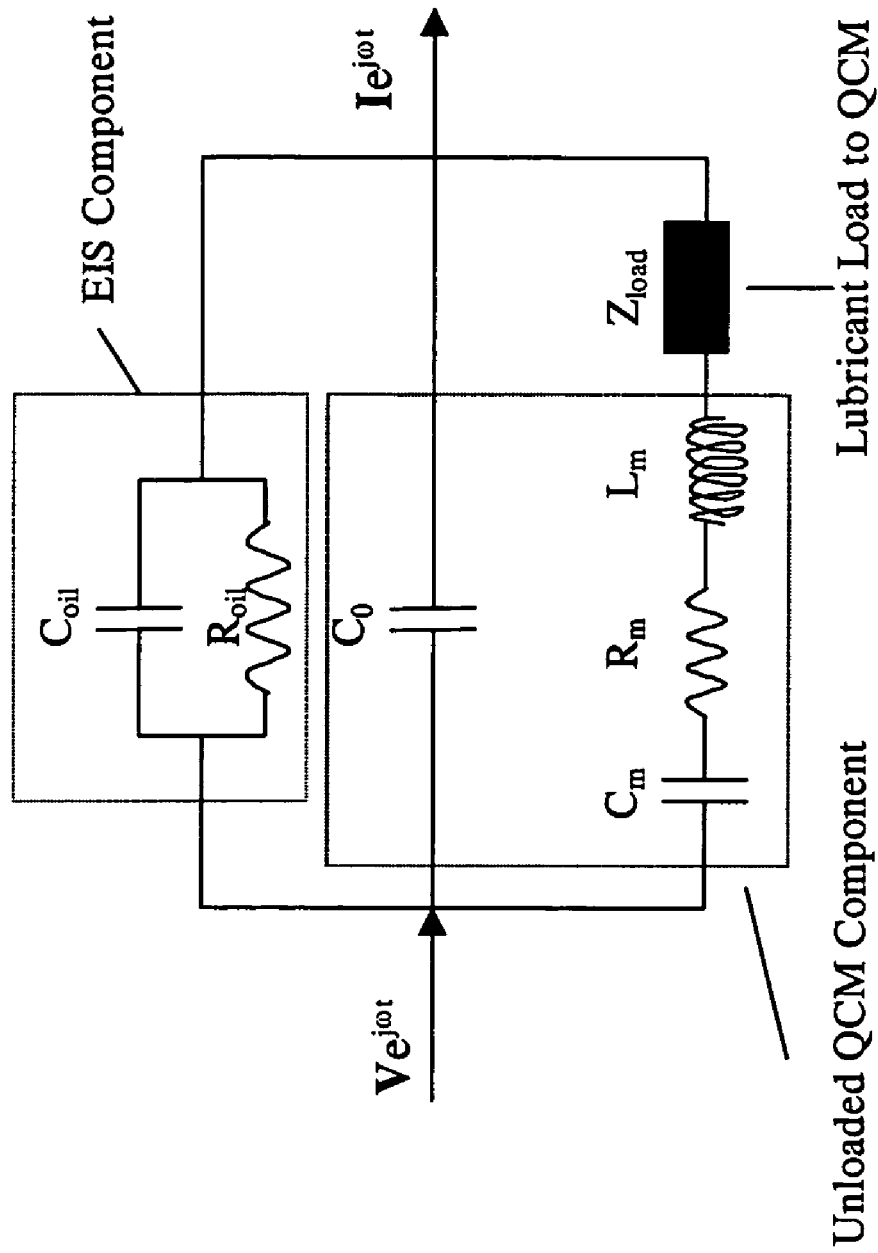
FIG. 2 is an electric circuit model that represents the electrical behavior of the sensor of the invention.

It is common practice to use an equivalent electrical circuit model to represent the electrical behavior of a sensor. When the frequency of the AC voltage excitation to the sensor 10 of the invention is close to the resonance of the QCM crystal 13, the equivalent circuit shown in FIG. 2 might be used to approximate the electrical behavior of the sensors 10. The impedance measurement is total impedance that includes contributions from both EIS and QCM components. Therefore, it is necessary to separate the impedance contribution from each other.

The impedance contribution from the EIS component represents the impedance of the bulk liquid that is often approximated by a parallel RC circuit. The capacitance, $C_{oil}$, measures the dielectric constant of the liquid and the resistance, $R_{oil}$, the resistance to the ion conductance. The resistance is a complex function of the ion concentration and mobility. For lubricant oil, experimental data indicated that $R_{oil}$ is strongly correlated with the viscosity and ion concentration in lubricant. For ideal lubricant fluid in which all ions are free particles and obey the classical Stokes' law under external electric field, the liquid resistance can be written as $$R_{oil} = c \frac{\eta}{\chi} \quad (2.1)$$

where $\chi$ is the concentration of ions in the lubricant and $\eta$ is the viscosity of the lubricant, and c is a proportional constant. The actual relationship between the resistance and the lubricant properties are more complicated than equation (2.1). But it is generally true that $R_{oil}$ increases with the viscosity of the lubricant and decreases with the ion concentration. For the lubricant with charged additive, $R_{oil}$ increases when additive is depleted.

The capacitance $C_{oil}$ is sensitive to water contamination because the dielectric constant of water is much higher than that of the typical lubricant. Therefore, it is useful for detect water content in the lubricant.

The impedance contribution from QCM component of the sensor represents the impedance of the crystal loaded with the liquid. A parallel circuit can also be used to approximate this impedance. The motional arm of this circuit is what causes the mechanical resonance of the crystal vibration. Without liquid load, the resonance circular frequency is given by $$\omega_0 = \frac{1}{\sqrt{L_m C_m}} \quad (2.2)$$

and damping to the resonance comes from the resistance, $R_m$. However, when the crystal is subject to the liquid, the liquid loading affects the vibration of the crystal by two factors. One factor is additional mass of a very thin film of the liquid adhered to the surface of the crystal which will reduce the resonance frequency. And another factor is additional viscous damping, which reduces the surface vibration amplitude. Electrically, this loading effect can be represented by an additional impedance term, $Z_{load}$. It is this term that we would like to measure in order to estimate the viscosity of the liquid. If expressing this impedance load by $$Z_{load} = \delta R + j\omega \delta L \quad (2.3)$$

where $\omega$ is the circular frequency, then the resonance frequency would be changed to $$\omega_r = \frac{1}{\sqrt{(L_m + \delta L) C_m}} \quad (2.4)$$

and damping to $R_m + \delta R$. Theoretical vibration analysis of the crystal in viscous fluid shows that $$\delta\omega_r = \omega_r - \omega_0 = -a\omega_0^{3/2}\sqrt{\rho\eta} \quad (2.5)$$

and $$\delta R = b\omega_0^{-1/2}\sqrt{\rho\eta} \quad (2.6)$$

where $\rho$ is the density of the liquid, and a and b are proportional constants that depend on the properties and design of the crystal.

It should be noted that either $\delta\omega_r$ or $\delta R$ actually measures the product of density and viscosity of the liquid, not the viscosity alone. However, very often, the change in the density of the lubricant oil as it ages is small compared with the change in viscosity. Therefore one may use those measurements to estimate the viscosity of the lubricant.

Measurement Method

If one excites the sensor with a small AC voltage, $Ve^{j\omega t}$, and measures the current flowing through the sensor, the input electrical impedance of the sensor is $$Z = \frac{V}{I} \quad (3.1)$$

where V is the amplitude of the excitation voltage, and I is the complex amplitude of the current through the sensor. However, it is convenient to analyze the sensor with input electrical admittance, which is simply $$Y = \frac{1}{Z} = G + jB \quad (3.2)$$

in which G and B are electrical conductance and susceptance. Using the equivalent circuit in FIG. 2 and solving for the complex admittance yields $$G = \frac{1}{R_{oil}} + \frac{R}{R^2 + X^2} \quad (3.3)$$

$$B = \omega(C_{oil} + C_0) - \frac{X}{R^2 + X^2} \quad (3.4)$$

where the motional resistance and reactance of the loaded crystal are $$R = R_m + \delta R \quad (3.5)$$

$$X = \omega(L_m + \delta L) - \frac{1}{\omega C_m} \quad (3.6)$$

With some mathematical manipulation of equation (3.3) and (3.4), one can derive the following relationship between G and B:

$$\left(G - \left(\frac{1}{R_{oil}} + \frac{1}{2R}\right)\right)^2 + (B - \omega(C_{oil} + C_0))^2 = \left(\frac{1}{2R}\right)^2 \quad (3.7)$$

Figure 3:
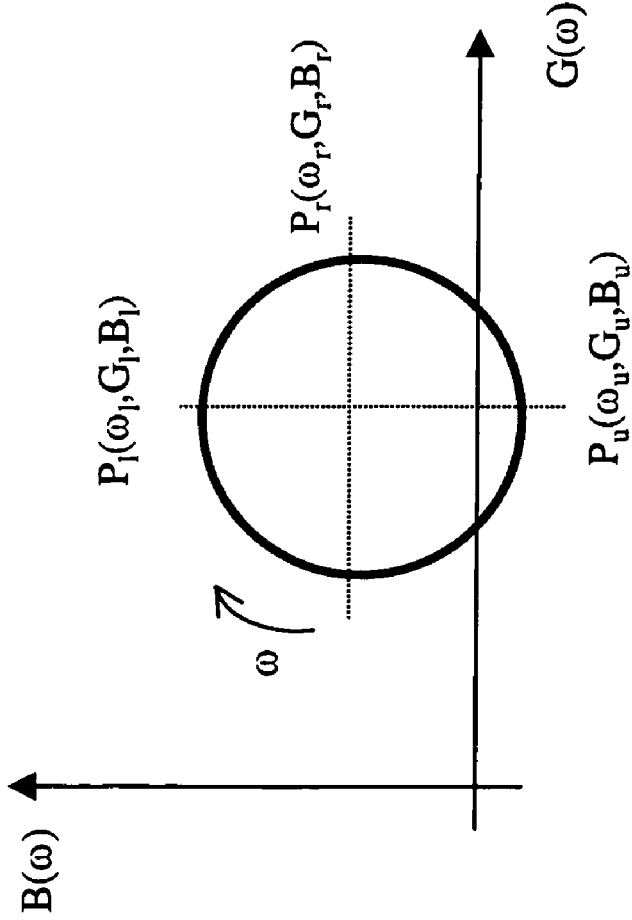
FIG. 3 is a Nyquest plot of complex admittance.

The plot of G verse B as functions of frequencies, often called Nyquest Plot, is a clockwise loop as shown in FIG. 3. If the mechanical resonance of the crystal is reasonably sharp, this loop is very close to being a circle.

There are three important points on the circle as shown on FIG. 3: the mechanical resonance point $P_r$ and two half-power points, $P_l$ and $P_u$, at which the vibration power of the crystal is half of that of the resonance. The values of G and B at those three points are also shown on FIG. 3.

A closer look into the characteristics of Nyquest plot on FIG. 3 reveal two important observations:

1. Though the Nyquest loop requires an infinite number of frequency points, the properties of the sensor can be completely determined by measuring the input electrical conductance and susceptance at any two of three feature points: $P_r$ (resonance) and two half-power points $P_l$ and $P_u$ of the loop.

Figure 4:
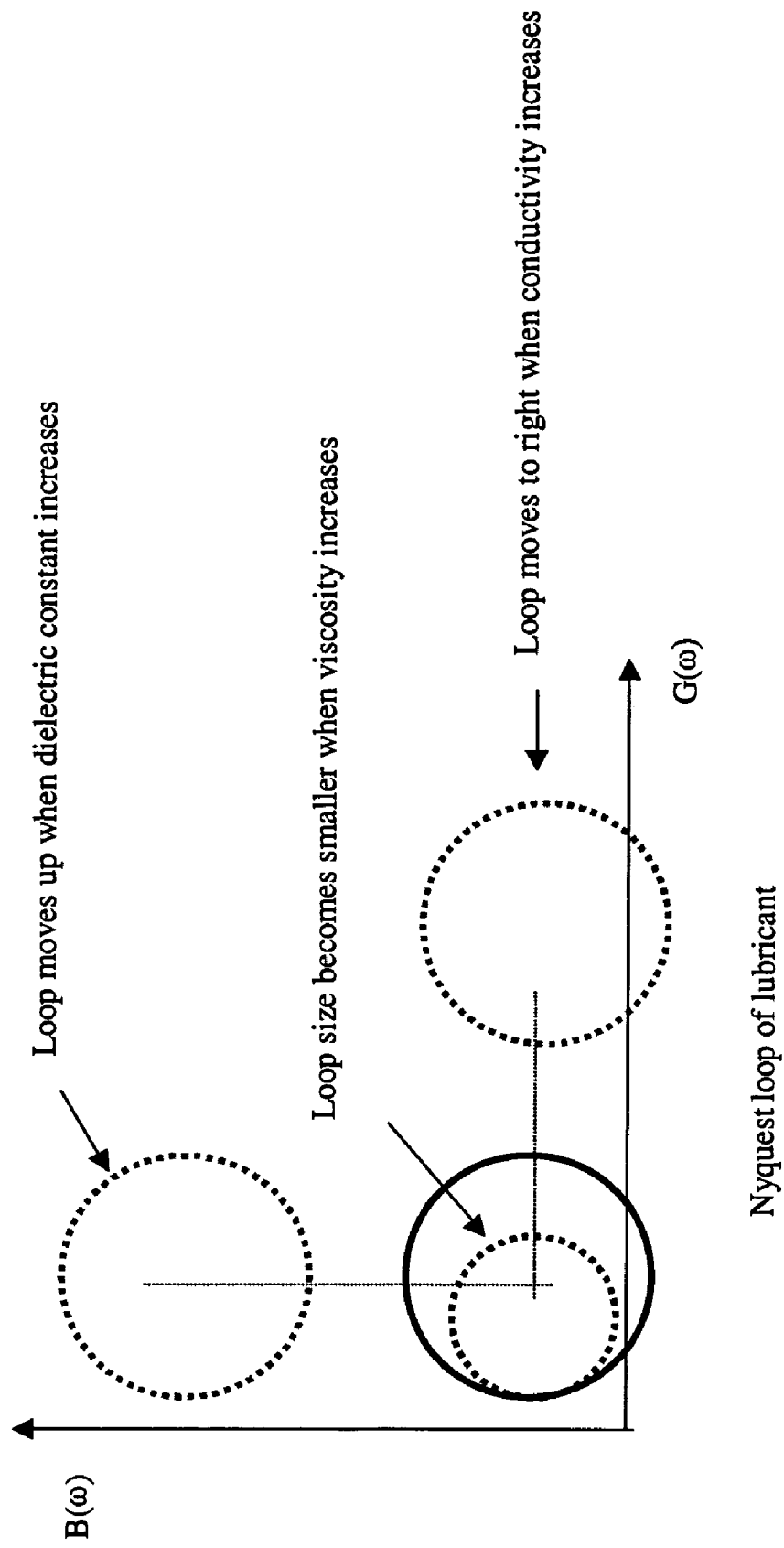
FIG. 4 is an illustration of the effects of viscosity, conductivity and dielectric constant of a lubricant on a Nyquest loop obtained according to the invention.

2. The impedance loading of the lubricant on the crystal alone determines the size of the Nyquest loop. The bulk impedance of the liquid (resistance and capacitance) only affects the position of the loop. As illustrated in FIG. 4, this provides a straightforward way to separate the measurements for determination of the electrochemical and viscoelastic properties of the liquid.

The discussion which follows will demonstrate the procedure of the electrical property computation with admittance measurements at $P_r$ and $P_l$.

Lubricant Loading Resistance δR on Crystal

The total motional resistance is reciprocal of the diameter of the Nyquest circle can be determined from the following relation $$G_r - G_l = \frac{1}{2R} \quad (4.1)$$

Recalling equation (3.5), one can compute the resistance due to the liquid loading on the crystal is $$\delta R = \frac{1}{2(G_r - G_l)} - R_m \quad (4.2)$$

provided that $R_m$ is known from calibration of the unloaded QCM.

Liquid Loading Inductance δL of Crystal

From the definition of the resonance frequency from equation (2.4), one can estimate the inductance loading by $$\delta L = \frac{1}{\omega_r^2 C_m} - L_m \quad (4.3)$$

Liquid Bulk Resistance $R_{oil}$

The liquid bulk resistance changes the position of the Nyquest loop along the G axis in FIG. 4. Higher resistance would move the circle to the left and lower resistance to the right. The following relation can determine the bulk resistance of the liquid $$G_r - \frac{1}{R} = \frac{1}{R_{oil}} \text{ or} \quad (4.4)$$

$$R_{oil} = \frac{1}{2G_l - G_r} \quad (4.5)$$

Liquid Bulk Capacitance $C_{oil}$

The liquid bulk capacitance changes the position of the Nyquest loop along the B axis of FIG. 4. Larger capacitance would move the circle up and lower capacitance down. The following relation can determine the bulk capacitance of the liquid $$B_r = \omega_r(C_{oil} + C_0) \quad (4.6)$$

so that $$C_{oil} = \frac{B_r}{\omega_r} - C_0 \quad (4.7)$$

An alternative procedure would be using the admittance measurements at two half-power points $P_l$ and $P_u$ at which motional reactance is maximum and minimum respectively. The electrical properties of the sensor can be determined with the following relations $$\delta R = \frac{\omega_l + \omega_u}{(\omega_l + \omega_u)(B_l - B_u) - (\omega_l - \omega_u)(B_l + B_u)} - R_m \quad (4.8)$$

$$R_{oil} = \frac{2(\omega_l + \omega_u)}{(\omega_l + \omega_u)(G_l + G_u - B_l + B_u) - (\omega_l - \omega_u)(B_l + B_u)} \quad (4.9)$$

$$C_{oil} = \frac{B_l + B_u}{\omega_l + \omega_u} - C_0 \quad (4.10)$$

According to the invention, therefore, the frequency impedance data or admittance data obtained as described herein for the fluid being monitored is then compared to a predetermined value or values, as the case may be, to determine the condition of the fluid being analyzed. Indeed the measured values may be used to provide a visual display such as an indication of the remaining useful life of the lubricant. Alternatively, a signal, such as an alarm or bell may be provided when the monitored fluid condition reaches a predetermined state requiring changing of the fluid before continuing operation of the mechanical system.

EXAMPLES

The invention will be further illustrated by using prepared mixtures of glycerol and water as test fluids. Glycerol and water mixtures are selected because of significant difference in the viscosity and dielectric constant between glycerol and water. At room temperature, the viscosity of the glycerol is about 1500 times of that of the water. The dielectric constant of the glycerol is about half of that of the water. As the content of glycerol is increased, the viscosity of the mixture increases and the dielectric constant decrease.

The invented sensor (denoted as EISQCM in data plots) in the test was constructed by modifying an off-the-shelf 5 Mhz QCM sensor. A third electrode (EIS counter electrode) was added to QCM holder as described in FIG. 1. A Soltran Impedance Spectrum Analyzer was used for the impedance measurement. The analyzer measures the electrical impedance by inputting a sinusoidal excitation voltage of constant amplitude to the work electrode of the sensor and measuring the resultant current from a counter electrode. By linearly sweeping a frequency range from 4.95 to 5.025 MHz with a step length of 250 Hz, the analyzer produces an impedance spectrum with real and imaginary parts at each frequency point (total about 300 points in the spectrum). The impedance spectrum is then converted into the admittance spectrum and the electrical properties are extracted by using the equivalent electric circuit model and data analysis technique described previously.

Since EISQCM has three electrodes, the same sensor is configured as either EISQCM, or EIS, or QCM by connecting different electrodes to the impedance spectrum analyzer. This provides a way to compare the output of the EISQCM with those of the QCM and the EIS for each mixture and validate the capability of the EISQCM as an integrated sensor.

Figure 5:
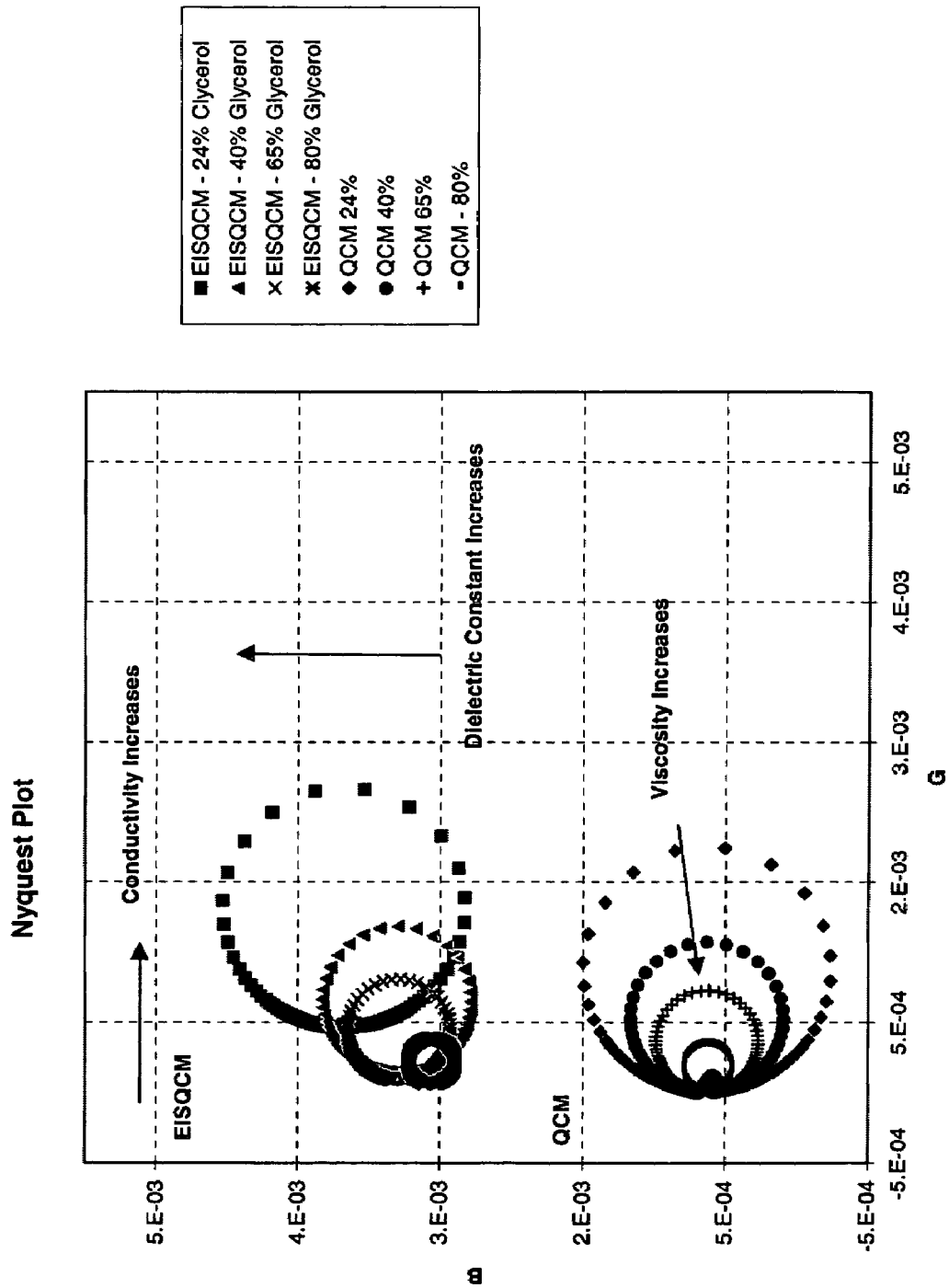
FIG. 5 is a comparison of Nyquest loop plots of test liquids from impedance measurements made with a sensor of the invention and with a QCM sensor.

FIG. 5 presents the Nyquest loops (G-B plot) from the impedance measurements of the EISQCM and the QCM sensor configurations. Qualitatively, the size of Nyquest loop from the EISQCM remains the same as that of the QCM, indicating that the EISQCM measures the viscosity effect as well as the QCM does. Higher content of glycerol reduces the loop diameter as expected from higher viscosity effect. However, the center locations of he Nyquest loops from the EISQCM are different from those of the QCM, indicating that the EISQCM provides additional information on the electrochemical properties of the mixture. Higher content of glycerol lowers the loop center along B axis due to lower dielectric constant, and moves the loop further to the left along G axis due to lower mixture conductivity.

Figure 6:
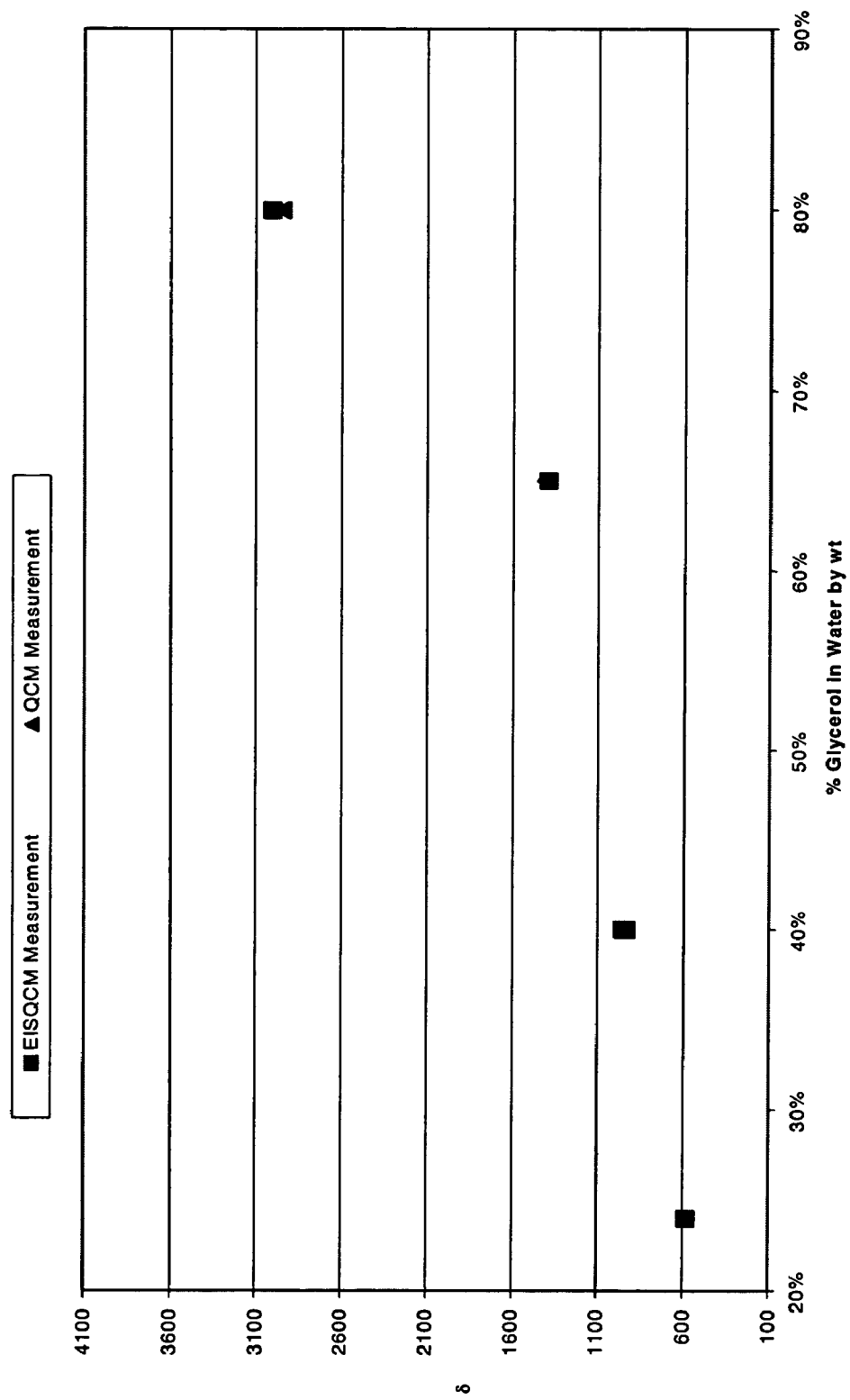
FIG. 6 is a comparison of liquid resistance loading on a crystal as a function of glycerol content in water obtained from the impedance measurements using a sensor of the invention and using a QCM.

FIG. 6 presents the plots of the liquid resistance loading on the crystal or viscous damping to the crystal vibration as a function of glycerol content in water, extracted from the impedance measurements of the EISQCM and QCM sensor configurations. Comparison of the two sensors shows that the results are almost identical and the resistance increases with the content of glycerol in water or liquid viscosity as expected.

Figure 7:
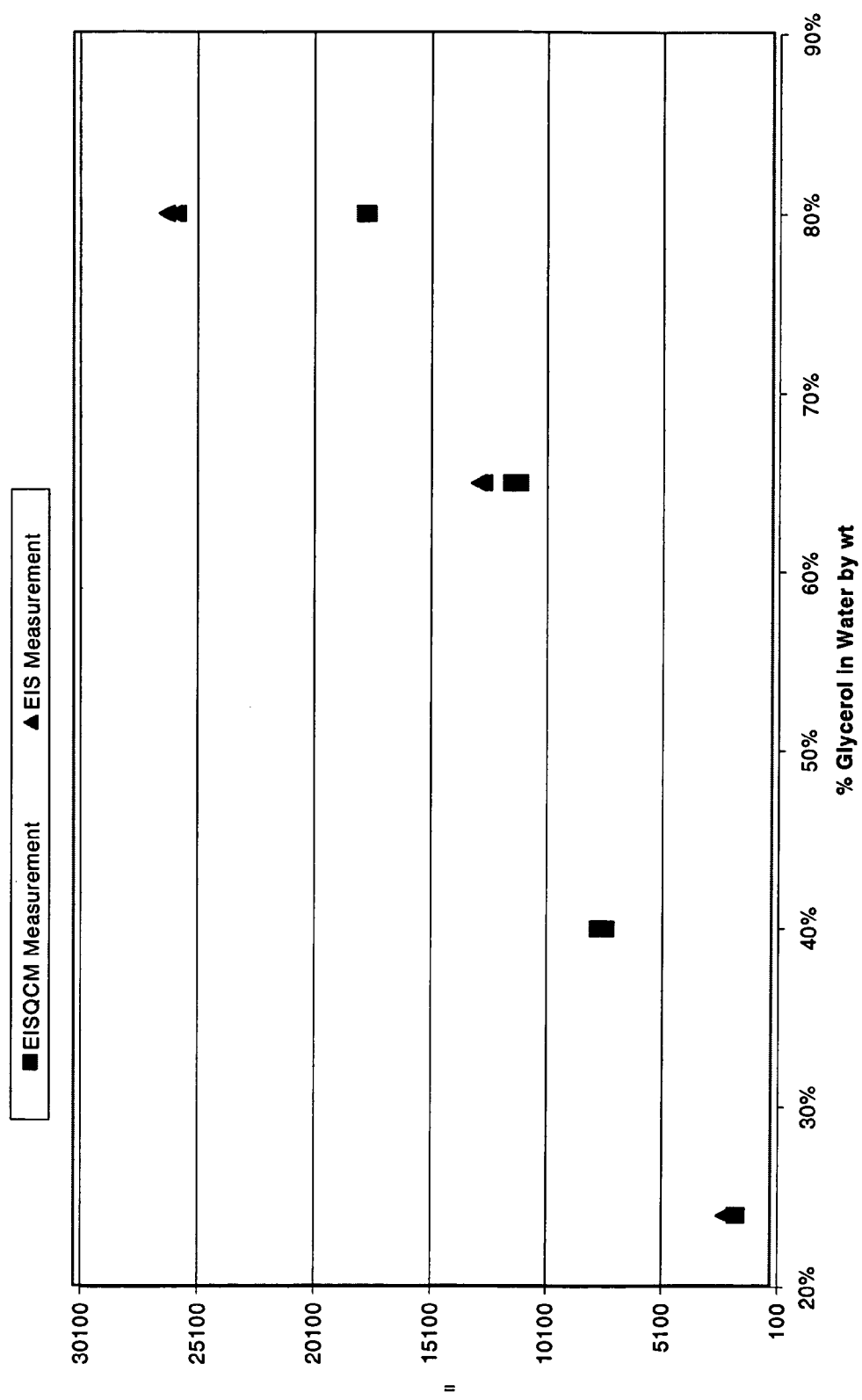
FIG. 7 is a comparison of liquid bulk resistance as a function of glycerol content in water obtained from the impedance measurements using a sensor of the invention and an EIS sensor.

FIG. 7 presents the liquid bulk resistance to ion conductivity as a function of the glycerol content in water, extracted from the impedance measurements of the EISQCM and EIS sensor configurations. The bulk resistance from the EISQCM is very close to those from the EIS except at very high concentration of glycerol (or very high viscosity). At very high viscosity, the liquid bulk resistance of the glycerol-water mixture is much higher than the liquid resistance loading on the QCM crystal (about 10 times higher), and the EIS component of the EISQCM is essentially "open circuit" or very small amount of current passes through the EIS component. As a result, it is expected that the signal-to-noise ratio in the EIS component is much lower and significant measurement error could arise.

Figure 8:
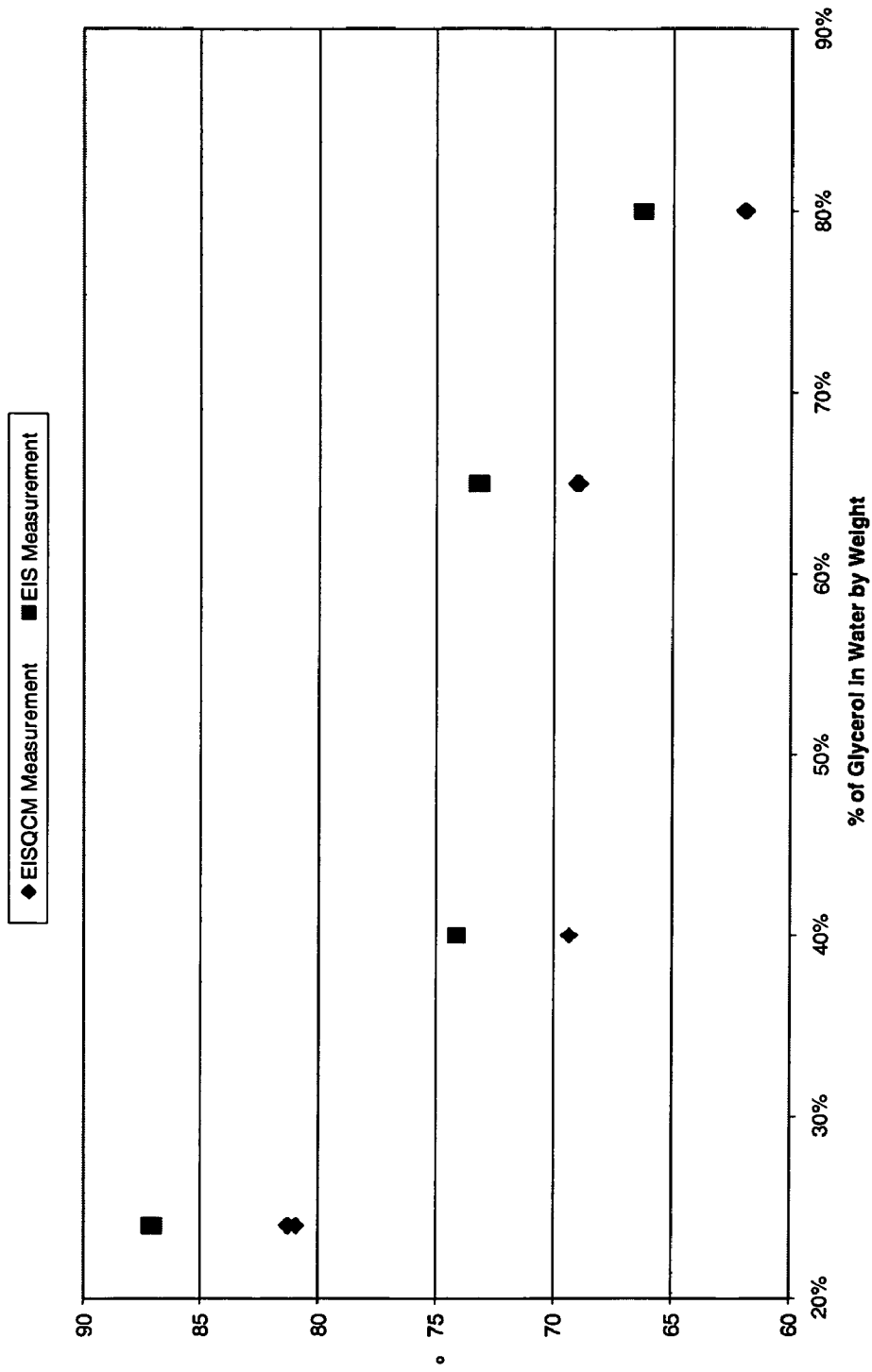
FIG. 8 is a comparison of the liquid bulk capacitance as a function of glycerol content in water obtained from impedance measurements using the sensor of the invention and using an EIS sensor.

FIG. 8 plots and compares the bulk capacitance of the mixture as a function of the glycerol content in water, as extracted from the impedance measurements of the EISQCM and EIS sensor configuration. Though the capacitance of the EISQCM follows the same trend as that of the EIS, there is a constant difference between the EISQCM and the EIS. The constant difference or bias is due to the fact that the capacitance of the EISQCM contains additional auxiliary capacitance due to extra electrical cables and fixtures.

What is claimed is:

1. A sensor for simultaneously monitoring the electrochemical and viscoelastic properties of a liquid comprising:
    an electrochemical impedance spectroscopy component (EIS) and a quartz crystal microbalance (QCM) component positioned within a housing for receiving a liquid for monitoring,
    the EIS and QCM components sharing a common electrode with the common electrode operatively connected to only one analyzer,
    the EIS component having an electrode spaced apart from the shared common electrode operatively connected to the analyzer defining a space to contain liquid received within the housing to be monitored; and
    the analyzer having means for simultaneously imposing an AC signal over a range of frequencies on both the EIS and OMS electrodes and measuring simultaneously the electrical response to the imposed signals whereby the electrochemical and viscoelastic properties of the liquid is monitored.

2. The sensor of claim 1 including means for comparing the electrical response to predetermined value or values whereby an indication of the condition of the liquid is obtained.

3. The sensor of claim 2 including means for generating an electrical signal when the electrical response exceeds the predetermined value.

4. A sensor for simultaneously monitoring the electrochemical and viscoelastic properties of a fluid comprising:
   a housing in which is positioned a quartz crystal having a top electrode and a bottom electrode;
   spaced apart from the top electrode is a third electrode defining a space therebetween for receipt of fluid to be monitored;
   mean for applying an AC signal to the electrodes and for measuring the electrical response to the applied signal whereby the electrochemical and viscoelastic properties of the fluid are monitored.

5. The sensor of claim 4 wherein the means for applying and measuring the applied signal is an impedance frequency analyzer.

6. The sensor of claim 5 wherein the crystal is an AT cut crystal.

7. The sensor of claim 6 including means for comparing the electrical response to predetermined value or values whereby an indication of the condition of the lubricant is obtained.

8. The sensor of claim 7 including means for generating an electrical signal when the electrical response exceeds the predetermined value.

9. A method for monitoring the condition of a lubricant comprising:
   passing the lubricant into contact with two spaced apart electrodes, one of the two electrodes being part of a quartz crystal microbalance, the quartz crystal microbalance having a second electrode;
   simultaneously applying an AC signal to the electrode at any two of: the mechanical resonance point, $P_r$, and half power points, $P_1$ and $P_u$, at which the vibration power of the crystal is half that of its resonance;
   simultaneously measuring the electrical response to the applied signal with only one analyzer;
   determining the conductance an susceptance from the electrical response; and
   comparing the measured conductance and susceptance to predetermined conductance and susceptance values whereby the condition of the lubricant is monitored.

10. The sensor of claim 1 wherein the analyzer is an impedence frequency analyzer.

11. The method of claim 9 wherein the analyzer is an impedance frequency analyzer.

12. The method of claim 9 further comprising predetermined conductance and susceptance values using equations:

$$G = \frac{1}{R_{oil}} + \frac{R}{R^2 + X^2}$$
$$B = \omega(C_{oil} + C_0) - \frac{X}{R^2 + X^2}.$$

* * * * *